US009952447B2

United States Patent
Haddadi et al.

(10) Patent No.: US 9,952,447 B2
(45) Date of Patent: Apr. 24, 2018

(54) METHOD FOR DETERMINING A BEHAVIOURAL, POSTURAL OR GEOMETRIC-MORPHOLOGICAL CHARACTERISTIC OF A PERSON WEARING SPECTACLES

(71) Applicants: Ahmed Haddadi, Charenton-le-Pont (FR); Jean Delzers, Charenton-le-Pont (FR)

(72) Inventors: Ahmed Haddadi, Charenton-le-Pont (FR); Jean Delzers, Charenton-le-Pont (FR)

(73) Assignee: ESSILOR INTERNATIONAL (COMPAGNIE GENERALE D'OPTIQUE), Charenton le pont (FR)

( * ) Notice: Subject to any disclaimer, the term of this patent is extended or adjusted under 35 U.S.C. 154(b) by 23 days.

(21) Appl. No.: 14/383,624

(22) PCT Filed: Mar. 8, 2013

(86) PCT No.: PCT/FR2013/000061
§ 371 (c)(1),
(2) Date: Sep. 8, 2014

(87) PCT Pub. No.: WO2013/132166
PCT Pub. Date: Sep. 12, 2013

(65) Prior Publication Data
US 2015/0049306 A1 Feb. 19, 2015

(30) Foreign Application Priority Data
Mar. 8, 2012 (FR) ...................................... 12 00705

(51) Int. Cl.
*G02C 7/02* (2006.01)
*A61B 3/00* (2006.01)
(Continued)

(52) U.S. Cl.
CPC ............ *G02C 7/027* (2013.01); *A61B 3/0008* (2013.01); *A61B 3/11* (2013.01); *A61B 3/111* (2013.01); *A61B 3/14* (2013.01); *G02C 13/005* (2013.01)

(58) Field of Classification Search
CPC ................ G02C 13/003; G02C 13/005; G02C 7/024–7/028; A61B 3/0008; A61B 3/11;
(Continued)

(56) References Cited

U.S. PATENT DOCUMENTS 5,402,199 A  3/1995 Akashi
5,617,155 A  4/1997 Ducarouge et al.
(Continued)

FOREIGN PATENT DOCUMENTS

EP  0 680 722   11/1995
WO  2008/009423   1/2008
(Continued)

OTHER PUBLICATIONS

International Search Report dated Jul. 19, 2013, corresponding PCT/FR2013/000061.

*Primary Examiner* — Marin Pichler
(74) *Attorney, Agent, or Firm* — Young & Thompson

(57) ABSTRACT

A method for determining at least one behavioral, postural or geometric-morphological characteristic of a person wearing spectacles, the method includes the steps of: a) illuminating the wearer's head using an infrared light source (220, 230, 240), b) acquiring an image of the wearer's head using an infrared image sensor (210); c) in the image, locating reflections from the infrared light surface, reflected by the two lenses of the spectacles; and d) using a computation unit (250) to deduce the required characteristic as a function of the positions of the reflections in the image.

21 Claims, 4 Drawing Sheets

(51) Int. Cl.
    *A61B 3/11*     (2006.01)
    *A61B 3/14*     (2006.01)
    *G02C 13/00*     (2006.01)

(58) Field of Classification Search
    CPC ........... A61B 3/111; A61B 3/113; A61B 3/14; A61B 3/145
    USPC .......... 351/206, 246, 204, 211, 208
    See application file for complete search history.

(56) References Cited

U.S. PATENT DOCUMENTS

| | | | |
|---|---|---|---|
| 6,922,494 B1* | 7/2005 | Fay | G01S 15/08 348/163 |
| 2006/0044509 A1 | 3/2006 | Fluegge et al. | |
| 2009/0021693 A1 | 1/2009 | Sessner et al. | |
| 2010/0128220 A1 | 5/2010 | Chauveau | |
| 2010/0177186 A1* | 7/2010 | Baranton | G02C 13/005 348/78 |
| 2010/0220285 A1* | 9/2010 | Simmonds | G02C 13/005 351/204 |
| 2011/0157550 A1* | 6/2011 | Chen | A61B 3/145 351/206 |
| 2011/0228975 A1 | 9/2011 | Hennessey et al. | |

FOREIGN PATENT DOCUMENTS

| | | |
|---|---|---|
| WO | 2008/132356 | 11/2008 |
| WO | 2009/024681 | 2/2009 |

\* cited by examiner

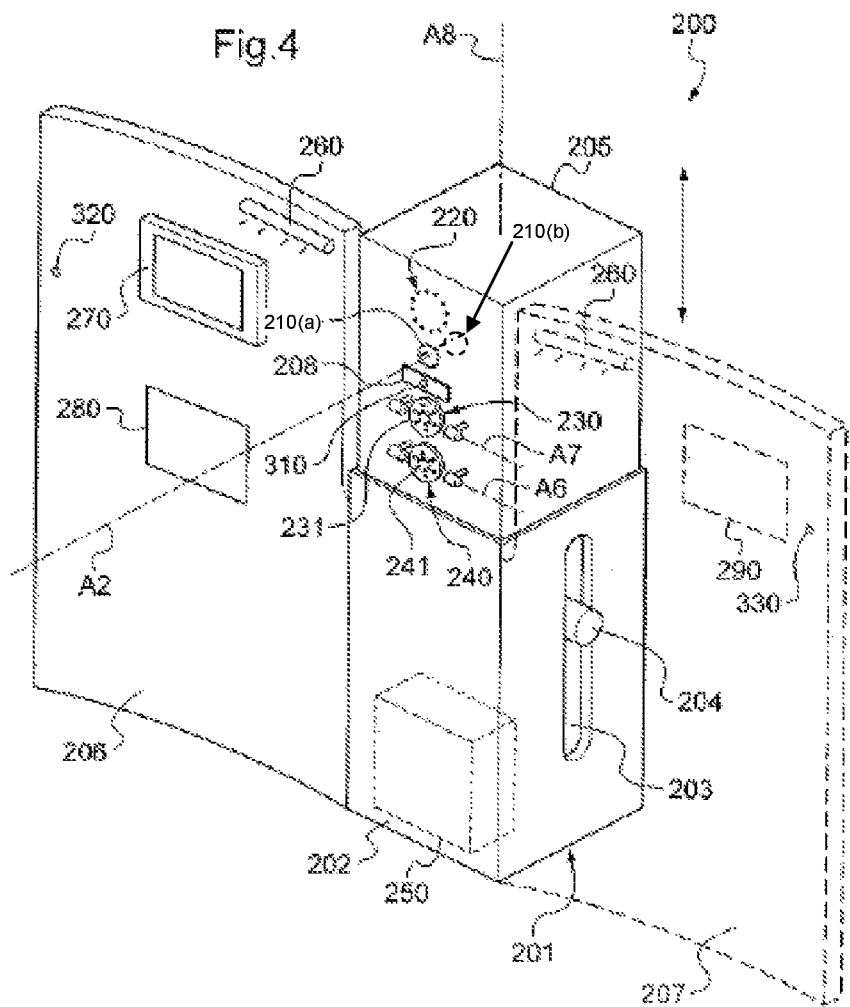

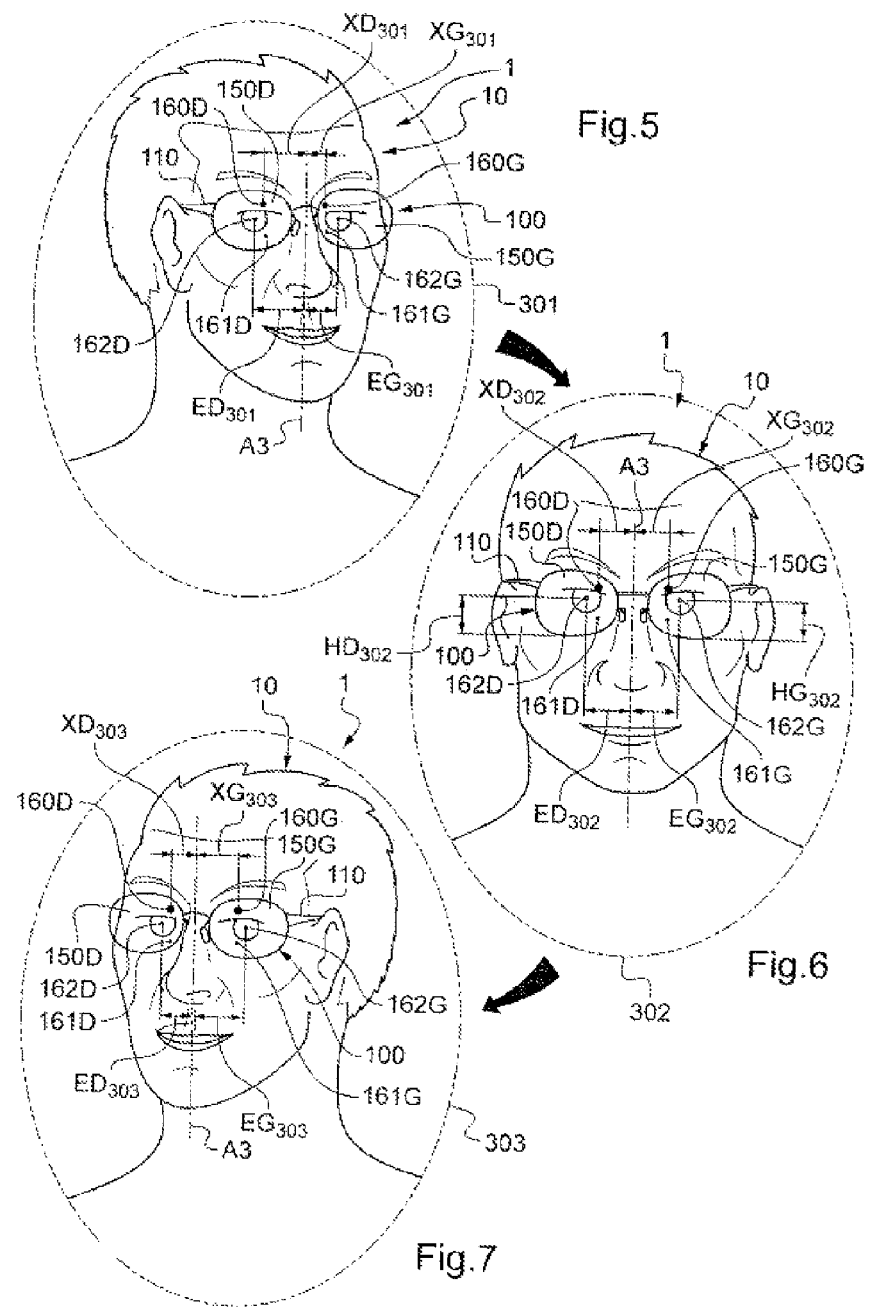

METHOD FOR DETERMINING A BEHAVIOURAL, POSTURAL OR GEOMETRIC-MORPHOLOGICAL CHARACTERISTIC OF A PERSON WEARING SPECTACLES

TECHNICAL FIELD OF THE INVENTION

Generally, the present invention relates to taking measurements of a subject.

It is particularly, but not exclusively, applicable to taking measurements of a spectacle wearer with a view to personalized optical design of corrective ophthalmic lenses tailored to this wearer.

It more particularly relates to a method and device for determining at least one characteristic for optimizing the wear position of a pair of spectacles on the face of the wearer, said optimizing characteristic being a geometrico-morphological, postural or behavioral characteristic of the wearer of a pair of spectacles.

PRIOR ART

During the design of a corrective ophthalmic lens, it is sought to take into account a large number of individual parameters, called personalized optical design parameters, attributed to the wearer and to the selected spectacle frame, in order to machine the lens such that it is tailored as best as possible to the wearer.

To determine these parameters, the optician places the selected spectacle frame on the nose of the wearer and performs various measuring operations on the wearer thus equipped. Thus, the optician may in particular determine the half pupillary distances of the wearer, i.e. the distances between the bridge of the nose of the wearer and each of the pupils of the latter.

A method for detecting the positions of two lenses in a spectacle frame is for example known from document WO 2008/009423, said method using two visible light sources and two image sensors. In this document, the lenses are pinpointed using stickers adhesively bonded to their front faces.

The image sensors are located facing the wearer. As for the two light sources, they are located above the spectacle wearer in order to illuminate the wearer without however generating reflections on the lenses, which would disrupt the measurements.

The light intensity emitted by the two light sources is then chosen to illuminate the face of the wearer so that the image acquired is correctly contrasted.

However, this method has various drawbacks.

Thus, it is necessary to adhesively bond the stickers to the lenses with care, which requires someone to be trained for this purpose.

Automatic location of the stickers is difficult to implement and has a significant failure rate, to the point that the optician is often forced to manually locate these stickers on the acquired image.

The stickers appear in the acquired image, which is not very esthetical and therefore not very flattering to the spectacle wearer who will see himself/herself in a mirror and on the acquired image.

The acquired images are moreover disrupted by ambient light that generates parasitic reflections on the lenses, which reflections are liable to hide the stickers.

In order to obtain a well contrasted image, the light intensity chosen generally dazzles the wearer. It would of course be possible to use a flash to remedy this drawback, but this would necessarily lead to the wearer start back, this movement being liable to corrupt the measurements.

Lastly, the method is inefficient for processing pairs of sunglasses, unless the tinted lenses are removed, which is at best tedious and at worst impossible in the case of rimless frames.

SUBJECT OF THE INVENTION

In order to remedy the aforementioned drawbacks of the prior art, the present invention provides a method for determining at least one geometrico-morphological, postural or behavioral characteristic of a wearer of a pair of spectacles, comprising steps of:

a) illuminating the head of the wearer using an infrared light source;

b) acquiring, via an infrared image sensor, an image of the head of the wearer illuminated by the infrared light source, in which image the pair of spectacles and the eyes of the wearer appear;

c) locating, in the image acquired in step b), reflections of the infrared light source reflected by the two lenses of the pair of spectacles and/or at least one corneal reflection of the infrared light source reflected by one of the two eyes of the wearer; and d) deducing by a processing unit said geometrico-morphological, postural or behavioral characteristic depending on the positions of the reflections and/or of said corneal reflection in said image.

By virtue of the invention, the wearer is not dazzled by the infrared light source while the measurements are being taken.

The infrared image sensor furthermore makes it easy to pinpoint the positions:

of reflections on the display lenses, since parasitic reflections are decreased in the infrared domain and it is possible to use a high light intensity without troubling the wearer, in order to distinguish the reflections of the light source from parasitic reflections; and of reflections on the pupils of the wearer, since, even when the lenses of the pair of spectacles are tinted, the pupils of the wearer will be visible under infrared light.

Moreover, the use of anti-reflection treatments on the lenses is not problematic insofar as these treatments are not designed to decrease reflections in the domain of infrared light.

By definition, a geometrico-morphological characteristic is here defined as a characteristic related to the shape of the face of the spectacle wearer.

It will for example possibly be a question of the interpupillary distance of the wearer, the distance between each pupil of the wearer and the bottom of the corresponding rim of the spectacle frame (referred to as "pupillary height") and/or of the distance between each eye of the wearer and the corresponding lens of the spectacle frame.

By definition, a postural characteristic is defined as a characteristic related to the position of the spectacle wearer in the measurement coordinate system.

It will for example be a question of the yaw angle between the sagittal plane of the head of the wearer and the optical axis of the camera, of the pitch angle between the Frankfurt plane of the head of the wearer and the optical axis of the camera, and/or of the roll angle of the head of the wearer about the optical axis of the camera.

By definition, a behavioral characteristic is defined as a characteristic related to the reactions of the wearer to a stimulus.

It will for example be a question of the propensity of the wearer to rather turn their eyes or head to observe an object as it appears in their field of vision.

The following are other advantageous and nonlimiting features of the determining process according to the invention:
- in step c), in the image acquired in step b), the reflections of the infrared light source reflected by the two corneas of the wearer are also located;
- in step b), said image is acquired in the domain of the near infrared, with a wavelength comprised between 780 and 1400 nm;
- said postural characteristic comprises a yaw angle, which separates the sagittal plane of the head of the wearer and the optical axis of the infrared image sensor;
- said geometrico-morphological characteristic comprises the half pupillary distances of the wearer;
- said geometrico-morphological characteristic comprises the pupillary heights of the wearer;
- in step b), the infrared image sensor acquires at least two images of the head of the wearer, in step c), said reflections are located in each image acquired in step b), and, in step d), said behavioral characteristic comprises a coefficient quantifying the propensity of the wearer to turn their gaze by moving rather their head or their eyes;
- said geometrico-morphological characteristic comprises the positions of the centers of rotation of the eyes of the wearer.

The invention also relates to a device for determining at least one geometrico-morphological, postural or behavioral characteristic of an individual, which comprises:
- at least one infrared light source suitable for illuminating the head of said individual;
- an infrared image sensor suitable for acquiring an image of the head of said individual illuminated by the infrared light source; and
- a processing unit suitable for locating on said image reflections of the infrared light source reflected by the pupils of said individual and/or by the two lenses of a pair of spectacles worn by said individual, and for deducing therefrom said geometrico-morphological, postural or behavioral characteristic.

The following are other advantageous and nonlimiting features of the determining device according to the invention:
- the processing unit is formed by a central processing unit of a computer and in which the infrared light source and the infrared image sensor are separate from the processing unit and are equipped with communicating means suitable for communicating with the central unit of the computer;
- provision is made for a supporting structure to which the infrared light source, the infrared image sensor and the processing unit are securely fastened;
- provision is made for a slide that is movably mounted on the supporting structure and that supports the infrared light source and/or the infrared image sensor;
- provision is made for a single light source movably mounted relative to said image sensor or for at least two light sources that are distant from each other in order to generate two separate reflections on said image;
- provision is made for means for motorizing the mobility of the slide, and in which said processing unit is suitable for automatically controlling said motorizing means to a position such that the face of said individual is visible to the infrared image sensor;
- each infrared light source is composed of at least one light-emitting diode;
- the infrared image sensor is also suitable for acquiring images in the visible domain;
- provision is made for a visible image sensor that is separate from the infrared image sensor and that is suitable for acquiring an image of the wearer in the visible domain;
- provision is made for means for displaying and/or printing the images acquired in the visible domain; and
- provision is made for means for acquiring at least one geometric characteristic of the spectacle frame.

DETAILED DESCRIPTION OF AN EXAMPLE EMBODIMENT

The following description, given with regard to the appended drawings, by way of nonlimiting example, will allow what the invention consists of and how it can be carried out to be understood.

In the appended drawings:

FIG. 4 is a schematic perspective view of a device suitable for implementing the method according to the invention;

FIGS. 5 to 7 show three images acquired by the image sensor in FIG. 3.

In the following description, certain references consist of a number followed by the letter G or D. These references then respectively designate elements located on the left or right relative to the spectacle wearer. The left and right eyes of the wearer are thus referenced 20G and 20D, respectively.

Figure 1:
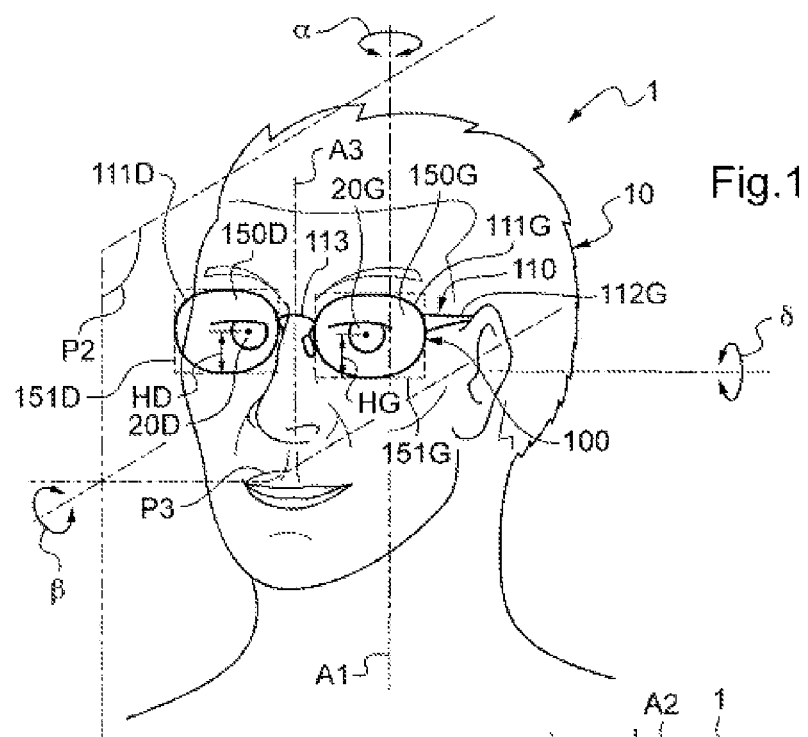
FIG. 1 is a schematic perspective view of the head of a spectacle wearer.

FIG. 1 shows the head 10 of an individual 1 wearing a pair of spectacles 100. This individual will be referred to below in the rest of the description as the "wearer".

In this description, reference will also be made to another individual, who will be referred to as the "vendor" and who will help the wearer 10 choose a pair of spectacles 100 and to measure the data required to manufacture the ophthalmic lenses (not shown) with a view to ordering them and fitting them in the spectacle frame 100 selected by the wearer.

Because the measurements are automated, this vendor does not have to be an optician.

Prior to the measurements, the wearer will choose a pair of spectacles 100 from the pairs of spectacles made available by the vendor.

During the measurements, the wearer will wear this pair of spectacles 100.

Figure 3:
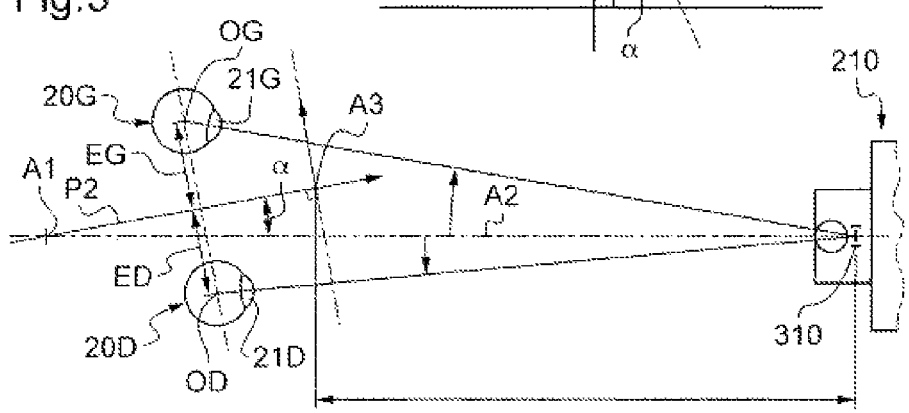
FIG. 3 is a schematic in which the eyes of the spectacle wearer in FIG. 1 and an image sensor are shown.

The wearer will either be sat or stood with their head 10 substantially straight and directed toward an image sensor 210 (see FIG. 3).

The vendor will moreover ask the wearer 1 to look at a target 310 located near the image sensor 210 (see FIG. 3). The centers of the two pupils 21G, 21D and the centers of rotation OD, OG of the two eyes 20G, 20D of the wearer 1 will therefore respectively be aligned with the target 310.

In FIG. 1, it may be seen that the pair of spectacles 100 chosen by the wearer 1 are full-rimmed spectacles (as a variant they could of course be any other type of spectacles, such as half-rimmed or rimless spectacles).

This pair of spectacles 100 comprises a spectacle frame 110 comprising two rims 111G, 111D (or eyewires) in which two display lenses 150G, 150D (intended to be replaced by the ophthalmic lenses tailored to the visual acuity of the wearer) are fitted.

The two rims 111G, 111D are connected to each other via a nose bridge or bridge 113 equipped with two nose pads resting on the nose of the wearer. They are also each equipped with a temple 112G, 112D resting on the corresponding ears of the wearer 1. These temples 112G, 112D each extend rectilinearly over most of their length, along a longitudinal axis, and are curved at their ends.

Each of the two rims 111G,111D of the spectacle frame 110 has, recessed into its internal side, a groove commonly called a bezel into which is fitted a bevel that protrudes from the edge face of the corresponding display lens 150G, 150D.

Figure 2:
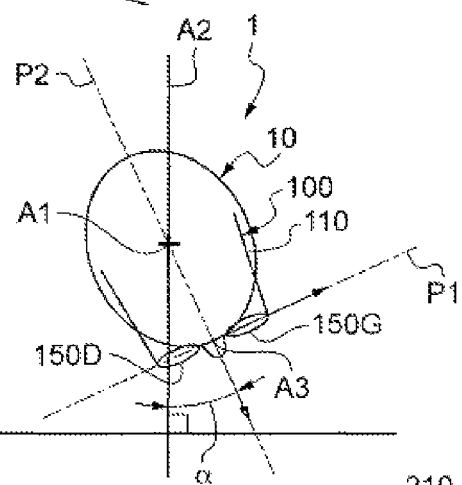
FIG. 2 is a schematic top view of the head of the spectacle wearer in FIG. 1.

As FIG. 2 shows, here a midplane P1 is defined relative to the spectacle frame 110, said midplane passing as close as possible to all of the points on the bottom edge of the bezels of the two rims 111G, 111D.

This midplane P1 is inclined relative to the plane passing through the longitudinal axes of the temples 112G, 112D by an angle called the "pantoscopic angle". On average, the pantoscopic angle of a spectacle frame is about 10 degrees.

As FIG. 1 shows, in each image of the wearer 1 acquired by the image sensor 210, the rims 111G, 111D of the spectacle frame 110 may be characterized by means of two boxes 151G, 151D defined according to the "boxing system".

These boxing-system boxes 151G, 151D are defined as rectangles circumscribing the rims 11G, 111D of the spectacle frame 110 (or the display lenses 150G, 150D), two sides of which are vertical and the two other sides of which are horizontal.

Then, in each image, an observable axis A3 of the spectacle frame 100 is defined as being the axis that is parallel to the vertical sides of the boxing-system boxes 151G, 151D, and that is located equidistant from the latter.

As FIG. 1 shows, a Frankfurt plane P3 is defined relative to the wearer 1, in the measuring position, as being the plane passing through the inferior orbital margins and the porion of the wearer (the porion being the highest point in the skull of the ear canal, which corresponds to the tragion of the ear). In the measuring position, this Frankfurt plane P3 will therefore be substantially horizontal.

A sagittal plane P2 is also defined as being the plane orthogonal to the Frankfurt plane P3 and to the axis passing through the centers of rotation OG, OD of the two eyes 20G, 20D of the wearer 1, and passing through the bridge of the nose of the wearer. Therefore, during the measurements, this sagittal plane P2 will be substantially vertical. Its position will be deduced not from the position of the nose of the wearer 1 but rather depending on the position of the pair of spectacles 100 worn by the wearer 1.

A longitudinal axis A1 is defined relative to the head 10 of the wearer 1 as being orthogonal to the Frankfurt plane P3, contained in the sagittal plane P2, and corresponding to the axis of rotation of the head 10 of the wearer 1 when the latter rotates their head from right to left (i.e. when they shake their head to say "no"). In the measuring position, this longitudinal axis A1 will be substantially vertical.

A frontal axis A4 is also defined as being the axis of intersection between the Frankfurt plane P3 and the sagittal plane P2.

A transverse axis A5 is also defined as being the axis perpendicular to the longitudinal A1 and frontal A4 axes.

In the measuring position, these two frontal and transverse axes A4, A5 will be substantially horizontal.

As FIG. 3 shows, the half pupillary distances EG, ED of the wearer 1 are defined as the distances separating the sagittal plane P2 from the centers of rotation OG, OD of the two eyes 20G, 20D of the wearer 1.

As FIG. 1 shows, the pupillary heights HG, HD of the wearer are for their part defined as the distances separating, in each acquired image, the centers of rotation OG, OD of the eyes 20G, 20D of the wearer 1 (which in practice are coincident in the image with the centers of the pupils 21G, 21D of the wearer 1) and the lower edge of the corresponding boxing-system box 151G, 151D.

Such as shown in FIG. 3, a horizontal plane and a vertical plane are moreover defined relative to the image sensor 210, the intersection of these planes being coincident with the optical axis A2 of the image sensor 210.

Ideally, it is then sought to place the head 10 of the wearer 1 so that its Frankfurt plane P3 is coincident with the horizontal plane of the image sensor 210 and so that its sagittal plane P2 is coincident with the vertical plane of the image sensor 210.

In practice, a slight offset between these planes, liable to corrupt the measurements, is generally observed.

This offset may be measured by means of three angles, namely roll angle $\beta$, pitch angle $\delta$ and yaw angle $\alpha$, which corresponds to the three ways in which the head 10 of the wearer 1 is free to rotate.

Thus, the yaw angle $\alpha$ will be defined as the angle of rotation of the head 10 of the wearer 1 about the longitudinal axis A1, between the ideal position of the head 10 of the wearer (facing the optical axis A2) and the actual position of the head 10 of the wearer. This yaw angle $\alpha$ will be measured in the horizontal plane of the image sensor 210.

The roll angle $\beta$ will be defined as the angle of rotation of the head 10 of the wearer 1 about the frontal axis A4 between the ideal position of the head 10 of the wearer and the actual position of the head 10 of the wearer. This roll angle $\beta$, will be easily measurable on each acquired image, depending on the inclination of the observable axis A3.

The pitch angle $\delta$ will be defined as the angle of rotation of the head 10 of the wearer 1 about the transverse axis A5, between the ideal position of the head 10 of the wearer (facing the optical axis A2) and the actual position of the head 10 of the wearer. This pitch angle $\delta$ will be measured in the vertical plane of the image sensor 210.

FIG. 4 shows the device 200 that allows the method according to the invention to be implemented and that, more generally, allows the data required to order the ophthalmic lenses to be fitted in the spectacle frame 110 selected by the wearer 1, in place of the display lenses 150G, 150D, to be measured and acquired.

This device takes the form of a spectacle kiosk 200, simultaneously playing the role of a spectacle frame display and a measuring center.

For this purpose it comprises at least one mounting 201, a light source 220, 230, 240, an image sensor 210 and a processing unit 250.

Preferably, the light source 220, 230, 240 emits in the infrared and the image sensor 210 captures infrared images.

The domain of the infrared that will be used here is the near infrared, the wavelengths of which are comprised between 780 and 1400 nm.

Specifically, using infrared light has a number of advantages. It especially allows parasitic reflections resulting from exterior or interior light that reflects on the display lenses 150G, 150D of the pair of spectacles 100 to be avoided. It also makes it possible to prevent the wearer 1 from being dazzled during the measurements. Lastly, it makes it possible for the eyes of the wearer 1 in the images acquired by the image sensor 210 to be seen even when the display lenses 150D, 150G are tinted.

The mounting could be a single part, such that the image sensor and the light sources are held immobile relative to the floor on which the spectacle kiosk stands. In this case, it would be necessary to provide a height adjustable stool so as to be able to place the wearer such that their head is located in the field of the image sensor.

In contrast, in the embodiment of the kiosk 200 shown in FIG. 4, the mounting 201 comprises a foot 202 that is placed on the ground, and a slide 205 that is mounted so as to move translationally relative to the foot 202 along a vertical axis A8 and that bears the light sources 220, 230, 240 and the image sensor 210.

The position of the image sensor 210 is thus adjustable in height depending on the size of the wearer 1.

The foot 202 more precisely has a hollow parallelepipedal shape that is elongate along the vertical axis A8 and that has a square horizontal cross section.

This foot 202 has a lower end that is closed by a wall placed on the ground, and an open upper end via which the slide 205 is inserted.

For this purpose, this slide 205 has a hollow parallelepipedal shape, with a horizontal cross section of outside dimensions equal to the inside dimensions of the foot 202, thereby allowing it to slide in the foot 202.

This slide 205 has a lower end that is open to the interior of the foot 202, and an upper end that is closed by a flat wall.

The slide 205 has, on two opposite sides, two protruding pins 204 that are inserted into two vertical oblong holes 203 produced in two opposite sides of the foot 202, in order to allow the slide 205 to be guided translationally along the vertical axis A8, between two (high and low) stop positions.

Provision is moreover made for motorized actuating means (not shown) allowing the slide 205 to be raised and lowered in the foot 202 to the desired height.

Provision is also made for means (not shown) for determining the height of the slide 205 in the foot 202 (for example an encoder wheel associated with a rack).

The mounting 200 moreover has two lateral wings 206, 207 that border its front face turned toward the wearer 1.

These two lateral wings 206, 207 are formed by vertical walls that are slightly curved forward and that are mounted on hinges on the two opposite sides of the foot 202 in which the vertical oblong holes 203 are provided.

The front faces of these wings 206, 207 are moreover equipped with hooks (not shown) on which the spectacle frames from which the wearer makes his/her choice rest.

In FIG. 4, it may be seen that the slide 205 bears at least two (here three) infrared light sources 220, 230, 240 suitable for illuminating the head 10 of the wearer 1 in the measuring position.

These light sources 220, 230, 240 are preferably distributed on either side of the image sensor, in the vertical plane of the image sensor 210.

These three light sources 220, 230, 240 are here mounted so as to be translationally immobile relative to the slide 205 and are formed of a plurality of light-emitting diodes (LEDs).

One of the light sources, called the main source 220, is located a small distance away from the image sensor 210 (i.e. here less than 10 cm from the image sensor). It is composed of a plurality of LEDs distributed in a circle. These LEDs are fastened directly to the slide 205. Such as shown in FIG. 4, this main source 220 is located above the image sensor 210.

The two other light sources, called secondary sources 230, 240, are located one above the other below the image sensor 210. They are each composed of a number of LEDs that is equal to the number of LEDs used in the main source 220, these LEDs being distributed in two concentric circles. They emit light of lower intensity than the intensity of the light emitted by the main source 220. The light intensities emitted by the secondary sources 230, 240 are, in the same way as the intensity emitted by the main source 220, adjustable.

These two secondary sources 230, 240 are fastened to bases 231, 241 that are mounted so as to be able to move rotatably relative to the slide 205 about two separate horizontal axes of rotation A6, A7. By virtue of this mobility, it is possible to manually direct these secondary sources 230, 240 toward the head 10 of the wearer 1.

The three light sources 220, 230, 240 are more precisely designed to form separate reflections on the display lenses 150G, 150D of the pair of spectacles 100 worn by the wearer 1.

Thus, when all the light sources 220, 230, 240 are reflected on the two display lenses 150G, 150D, the image sensor 210 may observe six glass-reflections.

Using three light sources 220, 230, 240 allows the image sensor 201 to see at least some of these reflections whatever the pitch angle δ of the head of the wearer 1. Specifically, it will be understood that when the wearer 1 inclines their head forward, the reflections seen by the image sensor 210 ride up and eventually leave the display lenses 150G, 150D.

The three light sources 220, 230, 240 moreover form a single reflection on each eye of the wearer 1, called the corneal reflection.

FIG. 6 shows a situation in which only two of the three light sources 220, 230, 240 reflect on the two display lenses 150G, 150D. Thus, four glass-reflections 160G, 160D, 161G, 161D, generated by the main source 220 and one of the secondary sources 230, and two corneal reflections 162G, 162D are observed on the two display lenses 150G, 150D. In contrast, the third light source 240 is too low, with regard to the pitch angle δ of the head of the wearer 1, to generate reflections on the display lenses 150G, 150D.

Of course, as a variant, provision could be made for the kiosk to comprise only one single infrared light source.

The latter could be immovably mounted in a preset position relative to the image sensor. It will then be preferable to use a light source that is quite large in size to generate a detectable corneal reflection. Moreover, this light source will have to be placed such that the two glass-reflections that it generates are located substantially halfway up the display lenses 150G, 150D (i.e. on the axis passing through the centers of the two boxing-system boxes of the frame) when the head 10 of the wearer 1 is ideally placed (Frankfurt plane P3 coincident with the horizontal plane of the image sensor 210 and sagittal plane P2 coincident with the vertical plane of the image sensor 210), taking into account the frame-average pantoscopic angle.

Thus, it will be recommended to check, during the measurements, that the pitch angle of the head of the wearer remains small, so that the image sensor can see the reflections of this light source on the display lenses.

According to another variant, provision will possibly be made for this single light source to be mounted so as to be translationally movable vertically relative to the image sensor, in order to compensate for the pitch angle of the head of the wearer.

Such as shown in FIG. 4, the kiosk 200 here comprises one single image sensor 210 with a horizontal optical axis A2.

Here, this image sensor is formed by a video camera 210 suitable for acquiring images in the near infrared and in the visible.

Here, this video camera is the Sony® video camera referenced: FCB-EX490. It is equipped with an infrared filter that can be switched between a normal position in which the latter filters infrared light so that the video camera 210 can acquire an image in the visible domain (called the "visible image" below), and a retracted position in which it allows infrared light to pass to the sensor, which can then acquire an image in the infrared domain (called the "infrared image" below).

This video camera is thus suitable for acquiring infrared images of the wearer, in which the glass-reflections and corneal reflections clearly appear, and visible images of the wearer allowing the latter to check that the selected pair of spectacles 100 suits him/her.

Of course, as a variant, provision will possibly be made not for just one video camera, but for two separate video cameras 210(a), 210(b), one suitable for acquiring infrared images and the other suitable for acquiring visible images.

Here, the front wall of the slide 205 contains a window closed by a one-way mirror, behind which the video camera 210 is located. Thus, the video camera 210 cannot be seen from the exterior of the kiosk 200, but it remains suitable for acquiring images of individuals placed in front of the kiosk 200.

The video camera 210 is then installed in the kiosk 200 such that its objective is located making contact with or near to the back face of this one-way mirror.

The objective of the camera 210 is moreover encircled by an opaque sidewall that prevents parasitic reflections from appearing in the acquired images.

In the present instance, all of the video camera is here housed in an opaque housing that is open to the front via an aperture through which the objective emerges, this housing being located in contact with the back face of the one-way mirror.

The spectacle kiosk 200 moreover comprises at least one target 310 located beside and a small distance away from the objective of the video camera 210, such that it may be seen by the wearer 1 in the measuring position.

Here, this target 310 comprises a window 208 produced in the wall of the slide 205, between the objective of the video camera 210 and the secondary sources 230, 240, through which an LED may be seen. In practice, this LED is here located in the foot 202 of the mounting 200 and is reflected toward the window 208 by means of a set of mirrors.

This target 310 allows the gaze of the wearer 1 to be drawn toward the objective of the video camera 210 during the measurements.

Provision is also made for two additional targets 320, 330, located on the exterior edges of each of the wings 206, 207 of the mounting 200, in the horizontal plane of the video camera 210.

As will be described in greater detail in the rest of this text, these additional targets 320, 330 will allow the gaze of the wearer 1 to be drawn in sequence toward one side of the kiosk 200 and then the other, in order to determine whether this wearer 1 has a propensity to turn their gaze by moving rather their head 10 or their eyes 20G, 20D.

Provision is moreover made for two fluorescent tubes 260, positioned on the upper edges of the two wings 206, 207 of the mounting 200, respectively, which illuminate the head 10 of the wearer 1 such that the visible images acquired by the video camera 210 are adequately exposed.

Provision is also made, in one of these two wings 206, for means for displaying 270 and means for printing 280 the visible images acquired.

Here, the displaying means consist of a touchscreen 270 fastened to the front face of the wing 206, so as to be visible to the wearer 1 in the measuring position.

As for the printing means, they are designed to print out sheets summarizing order data for ophthalmic lenses, on which the photos of the wearers appear.

Provision is moreover made for means for scanning the prescriptions of the wearer 1.

Here, the printing means and the scanning means are merged into one and consist of a single multifunction color printer 280 located in a housing provided recessed into the front face of the wing 206 of the mounting 200.

Of course, as a variant, it would also be possible to provide two separate apparatuses, one for printing the summarizing sheets and the other for scanning the prescriptions.

Lastly, provision is made, on the other of the two wings 207, for a means for acquiring at least one dimension of the pair of spectacles 100. Specifically, the images acquired by the video camera 210 do not allow the dimensions of the pair of spectacles 100 of the wearer 1 to be determined. Thus, it is necessary to scale the acquired images.

The aforementioned acquiring means 290 may take various forms.

Preferably, they comprise a barcode reader 290 connected to a database each record of which is associated with a spectacle frame model and comprises an identifier and data relating to this spectacle frame model.

In the present instance, the identifier of each record is formed by the number of the barcode that is assigned to the spectacle frame model.

As for the data memorized in each record, here they include:
  the total width of the spectacle frame of the model in question, measured between the two temples 112D, 112G;
  the ratio between the height and the length of the boxing-system boxes 151G, 151D of the rims of these spectacle frames; and
  the distance separating these two boxing-system boxes 151G, 151D.

Of course, the data memorized in each record of the database could include a smaller number of elements (for example only the total width of the spectacle frame) or a larger number of elements (for example the exact shape of the rims, the material of the spectacle frames, the pantoscopic angle and the face form angle of the spectacle frames, etc.).

As a variant, these acquiring means could comprise only a simple keyboard (a physical keyboard or a keyboard displayed on the touchscreen) allowing the vendor:
  to input the width of the selected spectacle frame 110, which he or she will have measured beforehand using a ruler; and
  to position, on the acquired image, two cursors at the two points between which he or she measured the width of the frame.

As yet another variant, these acquiring means could comprise only a simple gauge of known dimensions, to be attached to the selected spectacle frame (by clip fastening, adhesive bonding or any other means), in order to obtain, in each image acquired by the video camera, a reference the dimensions of which are known, thus allowing this image to be scaled.

As FIG. 4 shows, the processing unit 250 of the spectacle kiosk 200 is for its part housed in the foot 202 of the mounting 200. It is designed to control the various electronic components of the kiosk 200 and to process the images acquired by the video camera 210.

For this purpose, this processing unit 250 comprises a processor (CPU), a random access memory (RAM), a read-only memory (ROM), analog to digital (A/D) converters and various input, output and communications interfaces.

By virtue of its input interfaces, the processing unit 250 is suitable for receiving the images acquired by the video camera 210, the height of the slide 205 in the foot 202, measured by said determining means, and the barcode number of the selected spectacle frame, read by the barcode reader 290.

Thus, the processing unit 250 continuously stores these various data in its random access memory.

By virtue of a software program stored in its read-only memory, the processing unit 250 is suitable for implementing all of the method that will be described in the rest of this description. Thus, it is for example suitable for generating signals for controlling the means for actuating the swing 205 in order to position the latter at the desired height, and communications signals containing data for ordering ophthalmic lenses.

By virtue of its output interfaces, the processing unit 250 is suitable for transmitting these output signals to the various electronic components of the kiosk 200, especially to the video camera 210, to the light sources 220, 230, 240, to the touchscreen 270, to the multifunction printer 280, to the targets 310, 320, 330 and to the means for actuating the slide 205.

By virtue of its communications interfaces, the processing unit 250 is suitable for transmitting the communications signals to a center for manufacturing ophthalmic lenses. Lastly provision is made for a switch for powering up the kiosk 200.

Before the arrival of the wearer 1, the vendor powers up the kiosk 200 using the switch provided for this purpose.

During power-up, the control unit controls the electrical power supply of the fluorescent tubes 260 so as to illuminate the pairs of spectacles that are on display on the wings 206, 207 of the mounting 201 of the kiosk 200.

As for the three infrared light sources 220, 230, 240, they remain turned off.

Next, when an individual presents themselves, after having read a message on the screen inviting them to do so, he or she chooses a pair of spectacles 100 from all of those that are on display on the wings 206, 207 of the mounting 201 of the kiosk 200. In the example shown in the figures, the selected pair of spectacles is full-rimmed. Next, as invited to do so by a message displayed on the screen, the individual calls the vendor for the rest of the protocol.

Next, provision is made for an operation for determining a characteristic dimension of the selected spectacle frame 110.

As was described above, this operation is especially provided in order to allow the acquired images to be scaled.

During this operation, the vendor passes the barcode of the selected spectacle frame 110 in front of the barcode reader 290. The processing unit 250, by virtue of the barcode number, then searches in the database for the record corresponding to this spectacle frame 110, then it recovers and stores in its read-only memory the following data: the total width of the spectacle frame 110, the ratio between the height and the width of the boxing-system boxes 151G, 151D of the rims 111D, 111G of this spectacle frame 110, and the distance separating these two boxing-system boxes 151G, 151D.

Of course, as was described above, this barcode-reading operation could be replaced by a simpler operation consisting, for the vendor, in measuring the total width of the spectacle frame using a ruler, in inputting said width on a virtual keyboard displayed on the touchscreen, and in positioning on the acquired image two cursors at the two points between which the vendor measured the width of the frame (this operation for positioning the two points possibly as a variant being carried out automatically).

Provision is then made for an operation for acquiring prescriptions of the wearer 1 that the latter will have obtained beforehand at an optometrist.

These prescriptions are generally written on a prescription form and in particular include the type of lenses (single-vision, bifocal, progressive, tinted, etc.) and the refringent power that the lenses must have to correct the visual deficiencies of the wearer (i.e. their spherical, cylindrical and prismatic optical powers and their cylinder axes). They may of course include other information such as, in the case of bifocal or progressive lenses, an addition.

During this operation then, the vendor takes the prescription form and scans it using the multifunction printer 280 so that the processing unit 250 can store the scanned image of this prescription form in its read-only memory.

The vendor may also ask the wearer to choose the treatments that they would like on their ophthalmic lenses (antireflection, hydrophobic, etc.) and input this information into fields displayed for this purpose by the processing unit 250 on the touchscreen 270.

Once this information has been acquired, the processing unit 250 powers up the first target 310.

It also displays on the touchscreen 270:
- a message indicating that the measuring operations may commence;
- images acquired "in real time" by the video camera 210; and
- two arrows oriented in opposite directions, one pointing up and the other pointing down, for moving the slide 205 up or down.

The vendor then firstly invites the wearer 1 to put on their spectacles and to keep them on during all of the examinations that follow.

As will be described in detail in the rest of this description, these examinations will then allow the kiosk 200 to determine the half pupillary distances EG, ED and the pupillary heights HG, HD of the wearer 1, and advanced personalization parameters such as the distance VG, VD between the spectacle frame 110 and each eye of the wearer 1 (FIG. 8), the mobility behavior of their gaze, etc.

To do this, the vendor asks the wearer 1 to place themselves facing the kiosk 200, in the measuring position, and to look at the first target 310 while keeping their head straight, such that its Frankfurt plane P3 is substantially horizontal and its sagittal plane P2 is substantially vertical.

Here, the wearer 1 is invited to place themselves standing facing the slide 205 of the mounting 201 of the kiosk 200.

The vendor then adjusts the position of the slide 205 to a height suitable for the height of the wearer 1. For this purpose, he or she uses the arrows displayed on the touchscreen 270 to control the upward or downward motion of the slide 205 until it is at a height such that all of the face of the wearer 1 appears in the images acquired by the video camera 210 and displayed on the touchscreen 270.

Thus, in this position, all of the face of the wearer 1 is contained in the field of the video camera 210.

This operation for positioning the video camera 210 to the height of the head 10 of the wearer 1 could of course be carried out in another way.

Thus, it could be carried out automatically by the processing unit, which would process the images acquired by the video camera so as to discern therein the spectacle frame, and which would control the swing accordingly to a height such as to locate the spectacle frame at the center of the images acquired by the video camera.

As a variant, if the image sensor is not movably mounted relative to the ground, this positioning operation will possibly be carried out by asking the wearer to sit on a stool the height of which will have been adjusted beforehand.

Once this operation for positioning the wearer 1 relative to the video camera 210 has been carried out, the vendor initiates the taking of measurements by pressing on an ad hoc button displayed on the touchscreen 270.

The control unit 250 then turns on the three infrared light sources 220, 230, 240, to a nominal intensity.

Of course, the control unit could modulate this intensity, depending on the intensity of outside light, in order to prevent the latter from disrupting the measurements. However, using infrared light allows these disruptions to be limited, to the point that the nominal intensity is generally sufficient.

Using three separate light sources 220, 230, 240 then ensures the presence of at least one reflection on each display lens 150G, 150D of the pair of spectacles 100, provided of course that the wearer 1 does not turn their head right round.

In the variant where the kiosk comprises only one light source movable heightwise relative to the video camera, the operation for positioning the wearer facing the video camera would follow an automatic operation for positioning the light source. During this operation, the processing unit would vary the height of the light source and would process the images acquired by the video camera in order to immobilize the light source at the height at which the glass-reflections are centered on the display lenses.

Whatever the case may be, the vendor then asks the wearer 1 to turn their head 10 from right to left and from left to right, about the longitudinal axis A1 (so as to shake their head to say "no").

He or she is told that the movement must be made slowly (with a period longer than one second), with a small amplitude (about 10 degrees).

As a variant, provision could be made to mount the video camera and the light sources movably so that they pivot together about the longitudinal axis of the head of the wearer. Thus, the wearer would not have to move their head.

Next, when the wearer 1 starts turning their head in the requested way, the vendor presses on a button for initiating the measurements, said button being displayed on the touchscreen 270.

The video camera then acquires a plurality of infrared images, on which the head 10 of the wearer 1 and their pair of spectacles 100 appear.

The acquired images are first stored in the random access memory of the processing unit 250. Certain of the images, judged to be usable, are then selected by the processing unit 250 and stored in its read-only memory. The selection of the acquired images is carried out in the following way.

An acquired image may contain a plurality of glass-reflections (6 at most), each glass-reflection 160G, 160D, 161G, 161D is scored individually on various criteria, especially on its:

shape (width, height, width/height ratio); and
intensity (luminance).

Each pair of reflections (generated by a given light source and reflected by the two display lenses, respectively) is moreover scored according to other criteria, especially:

the distance between the reflections;
their horizontality relative to the horizontal axis of the boxing-system boxes; and
by comparison of the areas of the reflections.

Here, the score attributed to each criterion is not binary.
Provision may for example be made for it to vary continually between 0 and 1 such that:

it is equal to 1 if the criterion is comprised between 90% and 110% of its nominal value (preset and stored in the read-only memory of the processing unit 250);
it is equal to 0 if the criterion is higher than 120% or lower than 70% of its nominal value; and
it varies linearly between 70% and 90% and between 110% and 120%.

The criteria applied to the glass-reflections may also apply mutatis mutandis to the corneal reflections 162G, 162D. An additional criterion applying to the corneal reflections will be the distance separating each corneal reflection from the observable axis A3.

Thus, the chance of an image being selected increases with the product of the scores attributed to the various aforementioned criteria.

Provision may for example be made for the images selected to be those for which the product of the scores is higher than a preset threshold.

As a variant, provision may be made for the images selected to be those for which the products of the scores are the highest.

Moreover, provision may be made for an image to be automatically rejected if one of the scores attributed to it is lower than another preset threshold.

Thus, if, in an acquired image, the wearer 1 has their head turned by too large a yaw angle α and the glass-reflections are no longer present within the outline of the display lenses 150G, 150D, this image is automatically rejected.

Moreover, if, in an acquired image, the wearer 1 has their head inclined by too large a roll angle β and the glass-reflections generated by a given light source are offset in height on the two display lenses, this image will possibly be rejected if the offset is truly too large, or selected if the scores attributed to the other criteria are high.

The processing unit 250 thus obtains a limited number of infrared images usable in the rest of the method.

In this description, for the sake of clarity, the processing unit 250 will be considered to have selected only three infrared images 301, 302, 303—shown in FIGS. 5 to 7.

Preferably, the processing unit will stop the image acquisition when it has selected at least 10 different images.

Next, the processing unit 250 switches the infrared filter of the video camera 210 in order to store a visible image of the face of the wearer 1.

It simultaneously turns the infrared light sources 220, 230, 240 off and displays a message on the touchscreen 270 indicating to the wearer that they can stop turning their head.

This message is therefore displayed after the processing unit 250 has selected a preset number of images, here equal to 10.

As a variant, provision could be made to display this message after a preset length of time, for example equal to 10 seconds, deemed to be long enough to allow a large enough number of usable images to be obtained. The images could then possibly be selected subsequently, after all the images have been acquired.

Once the images 301, 302, 303 have been selected, the processing unit 250 calculates the yaw angle α of the head 10 of the wearer 1 in each of these images.

This yaw angle α is calculated by locating, in each image 301, 302, 303, the glass-reflections 160D, 160G, 161D, 161G relative to the sagittal plane P2 of the head of the wearer 1.

Here, this yaw angle α is more precisely determined by locating the glass-reflections 160D, 160G, 161D, 161G relative to the observable axis A3 of the spectacle frame (since its position substantially corresponds to the intersection of the sagittal plane P2 with the midplane P1 of the spectacle frame 110).

The position of the observable axis A3 of the spectacle frame 110 is obtained in 3 steps, consisting in:
locating in each image 301, 302, 303 the spectacle frame 110, and especially the rims 111D, 111G of this spectacle frame;
positioning on each image 301, 302, 303 the boxing-system boxes 151G, 151D; and
determining the position of the axis passing between these two boxing-system boxes, which in practice corresponds to the observable axis A3.

Here, using infrared light makes it easier to locate the spectacle frame 110, the outline of which stands out clearly from that of the face of the wearer 1.

Thus, the yaw angle α of the head 10 of the wearer 1 in each image 301, 302, 303 is calculated as a function of the distances separating the glass-reflections 160D, 160G, 161D, 161G from the observable axis A3.

Typically, as FIGS. 5 to 7 clearly show, the processing unit 250 determines in each image 301, 302, 303 the distances $XD_{301}$, $XG_{301}$, $XD_{302}$, $XG_{302}$, $XD_{303}$, $XG_{303}$ separating the observable axis A3 from the centers of the two largest glass-reflections 160G, 160D (the glass-reflections generated by the secondary sources being used only if the glass-reflections generated by the main source do not appear on the acquired images).

The yaw angle $α_i$ of the head 10 of the wearer 1 in each image 301, 302, 303 is then determined in the following way:

$$α_i = k \cdot (XG_i - XD_i)/(XG_i + XD_i), \text{ with } i \text{ ranging from 301 to 303.}$$

The coefficient k is then a constant related to the face form of the spectacle frame.

This coefficient k will possibly be formed by a preset and invariable constant, stored in the read-only memory of the processing unit 250. It will therefore always be the same whatever the spectacle frame selected by the wearer. This coefficient k will then possibly be determined experimentally on the basis of a representative sample of spectacle frames, and thus chosen to be equal to about 40°.

As a variant, this coefficient k will possibly be formed by a preset constant associated with the spectacle frame selected by the customer. In this variant, this coefficient k will then be determined experimentally for each spectacle frame model, then stored in the database so as to be accessible during the calculation of the yaw angle $α_i$ of the head 10 of the wearer 1.

This yaw angle could possibly be determined in another way.

By way of example, provision could be made to equip the spectacle frame with a system of reference points comprising easily pinpointable geometric features separated by a known real distance, and to determine the yaw angle as a function of the distance separating these geometric features in the acquired image (set beforehand to a 1:1 scale). Such a method is described in detail in document WO 2008/132356.

At this stage, the processing unit 250 has, stored in its memory, the yaw angles $α_{301}$, $α_{302}$, $α_{303}$ of the head 10 of the wearer 1 in each selected image 301, 302, 303.

The processing unit then determines the half pupillary distances EG, ED of the wearer 1 as a function of the positions of the corneal reflections 162G, 162D of the wearer 1 in at least one of the selected images 301, 302, 303.

It may do this in various ways. Two different methods are described here.

The first method consists in electing one image 302 from the selected images 301, 302, 303, namely that for which the calculated yaw angle $α_{302}$ is lowest, then in considering that in this elected image 302 the head 10 of the wearer 1 is face on. The half pupillary distances EG, ED will then possibly be read directly from this image 302.

However, this method requires a large enough number of images 301, 302, 303 to have been acquired and selected for, among these images, one of them to effectively show the head of the wearer 1 seen substantially face on.

This method is then more precisely implemented in the following way.

The processing unit 250 then locates in this elected image 302 the corneal reflections 162G, 162D, which are off-center relative to the glass-reflections.

Next, the processing unit 258 determines the distances $EG_{302}$, $ED_{302}$ separating the observable axis A3 from each of these corneal reflections 162G, 162D.

These distances $EG_{302}$, $ED_{302}$ are then scaled, thereby allowing the processing unit 250 to obtain the half pupillary distances EG, ED of the wearer 1.

The second method consists in considering all the selected images 301, 302, 303, then, using a statistical method, in evaluating the half pupillary distances EG, ED of the wearer 1.

This statistical method not only allows the half pupillary distances EG, ED of the wearer 1 to be evaluated, but also the eye/spectacles distances VG, VD separating the midplane P1 of the spectacle frame 110 and the centers of rotation OG, OD of the eyes 20G, 20D of the wearer 1.

This statistical method is then implemented on one of the two eyes 20G, 20D of the wearer 1.

Figure 8:
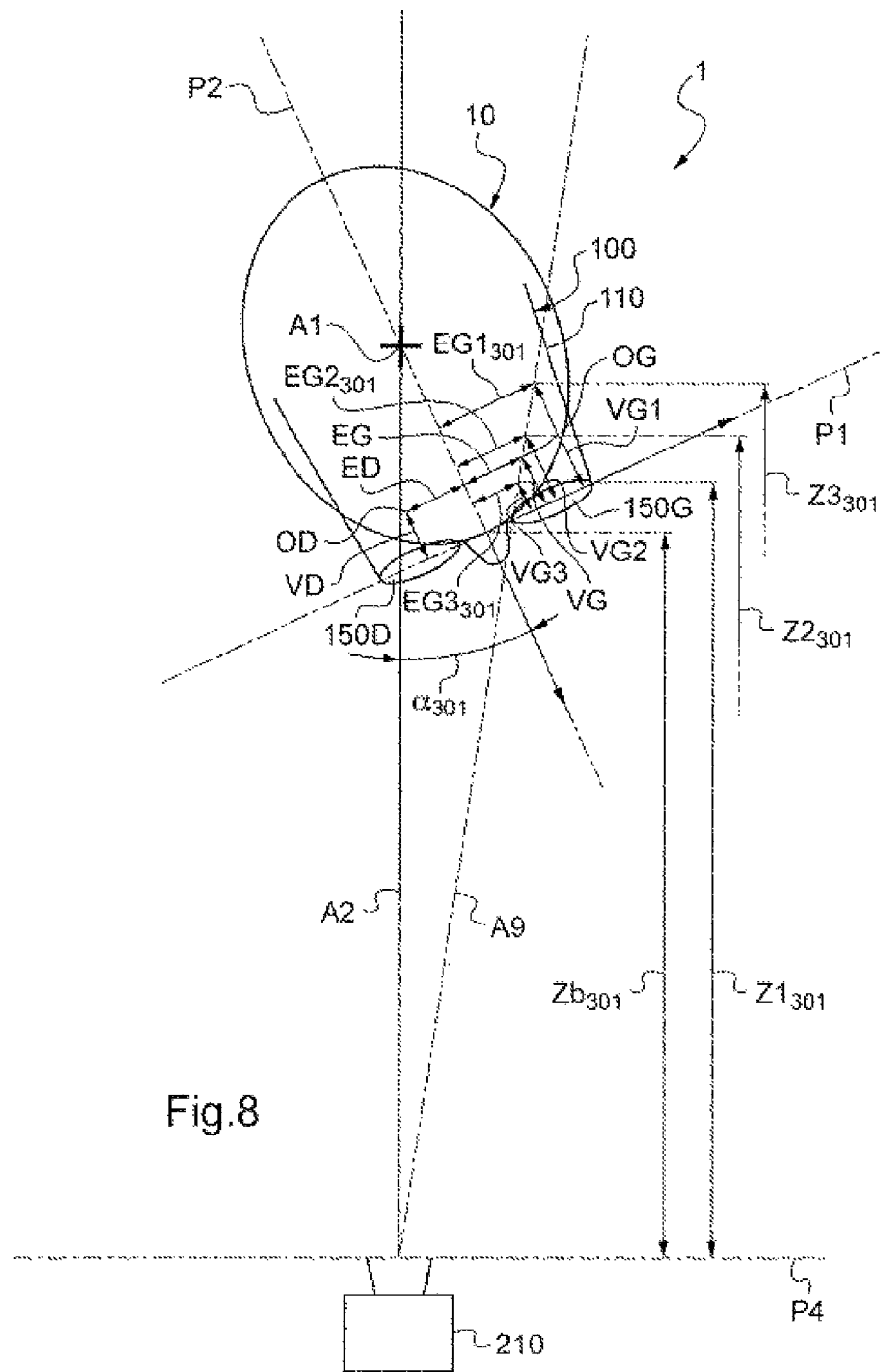
FIG. 8 is a schematic top view of the head of the spectacle wearer in FIG. 1.

Here, as shown in FIG. 8, the method will be implemented on the left eye 20G of the wearer 1 in order to determine his or her half pupillary distance EG and his or her left eye/spectacles distance VG.

Generally, the statistical method is based on the observation that, by virtue of the left corneal reflection 162G appearing in each image 301, 302, 303, the axis A9 (see FIG. 8) on which the center of rotation OG of the left eye 20G of the wearer 1 is located is known, and therefore all that remains to be determined is the position of the center of rotation OG on this axis A9.

This statistical method will then consist in:
simulating, in each image 301, 302, 303, a plurality of eye/spectacles distances VG1, VG2, VG3 (here 3 in number in order to make the description and drawings clearer);

determining the left half pupillary distance corresponding to each of these simulated distances (called the "simulated left half pupillary distance $EG1_{301}$, $EG2_{301}$, $EG3_{301}$, $EG1_{302}$, $EG2_{302}$, $EG3_{302}$, $EG1_{303}$, $EG2_{303}$, $EG3_{303}$"), then, as a function of all of these simulated left half pupillary distances;

determining which of the simulated eye/spectacles distances VG1, VG2, VG3 is closest to the actual eye/spectacles distance VG of the wearer 1.

More precisely, the processing unit 250 here considers three preset simulated eye/spectacles distances VG1, VG2, VG3 stored in its read-only memory. As a variant, and preferably, it will rather consider a number of simulated eye/spectacles distances higher than 10.

Then, for each of these simulated eye/spectacles distances, and for each of the acquired images (index i, varying in this example from 301 to 303), the processing unit 250 calculates iteratively (iteration index k varying from 1 to n):

$$Z1_{i,k}=Zb_i+VG1 \cdot \cos(\alpha_i)+EG1_{i,k-1} \cdot \sin(\alpha_i),$$

$$Z2_{i,k}=Zb_i+VG2 \cdot \cos(\alpha_i)+EG2_{i,k-1} \cdot \sin(\alpha_i),$$

$$Z3_{i,k}=Zb_i+VG3 \cdot \cos(\alpha_i)+EG3_{i,k-1} \cdot \sin(\alpha_i), \text{ where:}$$

$EG1_{i,0}$, $EG2_{i,0}$, $EG3_{i,0}$ set arbitrarily to a preset value, here chosen to be equal to 32.5 mm;

$Zb_i$ the distance separating the observable axis A3 and the general plane P4 of the objective of the video camera 210 in each image (and which is easily determinable, taking into account the width of the frame in the image considered relative to its actual width, and the yaw angle $\alpha_i$ of the head of the wearer);

$Z1_{i,k}$, $Z2_{i,k}$, $Z3_{i,k}$ the distances separating the simulated position from the center of rotation OG of the left eye 20G of the wearer 1 and the general plane P4 of the objective of the video camera 210.

If we denote:

$x_{OGi}$ and $y_{OGi}$: the coordinates, expressed in pixels, of the center of rotation OG in the image i, relative to the center of this image;

X, Y, Z: the coordinates, expressed in mm, of the center of rotation OG in the frame of reference of the video camera; and K, the size of a pixel, expressed in mm, for an object located one meter from the plane of the video camera.

Then, the following equations may be written:

$$X1_{i,k}=Z1_{i,k} \cdot K \cdot x_{OGi}$$

$$Y1_{i,k}=Z1_{i,k} \cdot K \cdot y_{OGi}$$

$$Z1_{i,k}=Z1_{i,k}$$

$$X2_{i,k}=Z2_{i,k} \cdot K \cdot x_{OGi}$$

$$Y2_{i,k}=Z2_{i,k} \cdot K \cdot y_{OGi}$$

$$Z2_{i,k}=Z2_{i,k}$$

$$X3_{i,k}=Z3_{i,k} \cdot K \cdot x_{OGi}$$

$$Y3_{i,k}=Z3_{i,k} \cdot K \cdot y_{OGi}$$

$$Z3_{i,k}=Z3_{i,k}$$

For the image i, the sagittal plane, denoted $P2_i$, may for example be defined as the plane that includes the following three points:

$A_i$: a point located on the observable axis A3, corresponding to the center of the segment connecting the two closest upper corners of the two boxing-system boxes 151G, 151D;

$B_i$: a point located on the observable axis A3, corresponding to the center of the segment connecting the two closest lower corners of the two boxing-system boxes 151G, 151D;

$C_i$: a point located on an axis that passes through the point $A_i$, that is perpendicular to the midplane P1 of the spectacle frame 110, and the coordinates of which in the frame of reference of the frame are such that the vector $A_iC_i$ has coordinates ($x_c$, $y_c$, $z_c$) where $x_c=0$ and $y_c=0$.

If we denote:

($x_{Ai}$, $y_{Ai}$) the coordinates of the point $A_i$ in the image i;

$X_{Ai}$, $Y_{Ai}$, $Z_{Ai}$, the coordinates of the point $A_i$ in the frame of reference of the video camera;

($x_{Bi}$, $y_{Bi}$) the coordinates of the point $A_i$ in the image i;

$X_{Bi}$, $Y_{Bi}$, $Z_{Bi}$, the coordinates of the point $B_i$ in the frame of reference of the video camera;

$X_{Ci}$, $Y_{Ci}$, $Z_{Ci}$, the coordinates of the point $C_i$ in the frame of reference of the video camera; and $M_i$, the three-dimensional rotation matrix describing the attitude of the frame in the space of the video camera (constructed from the angles $\alpha$, $\beta$ and $\delta$).

Then, as the distance of the observable axis A3 to the plane of the video camera P4 is known, $Z_{Ai}$ and $Z_{Bi}$ are known and the following equations may be written:

$$X_{Ai}=Z_{Ai} \cdot K \cdot x_{Ai}$$

$$Y_{Ai}=Y_{Ai} \cdot K \cdot y_{Ai}$$

$$X_{Bi}=Z_{Bi} \cdot K \cdot x_{Bi}$$

$$Y_{Bi}=Y_{Bi} \cdot K \cdot y_{Bi}$$

And, after inversion of the rotation matrix M:

$$(X_{Ci}-X_{Ai})=M^{-1}(0,0) \cdot x_c+M^{-1}(0,1) \cdot y_c+M^{-1}(0,2) \cdot z_c$$

$$(Y_{Ci}-Y_{Ai})=M^{-1}(1,0) \cdot x_c+M^{-1}(1,1) \cdot y_c+M^{-1}(1,2) \cdot z_c$$

$$(Z_{Ci}-Z_{Ai})=M^{-1}(2,0) \cdot x_c+M^{-1}(2,1) \cdot y_c+M^{-1}(2,2) \cdot z_c$$

As $x_c$ and $y_c$ are equal to zero by definition, it may be deduced therefrom that:

$$X_{Ci}=X_{Ai}+M^{-1}(0,2) \cdot z_c$$

$$Y_{Ci}=Y_{Ai}+M^{-1}(1,2) \cdot z_c$$

$$Z_{Ci}=Z_{Ai}+M^{-1}(2,2) \cdot z_c$$

Since the coordinates of the 3 points of the plane $P2_i$ are known, the latter is perfectly defined, and it is therefore possible to calculate using the conventional method the distance of any point in the plane $P2_i$.

In particular $EG1_{i,k}$, $EG2_{i,k}$ and $EG3_{i,k}$ may therefore be calculated, where:

$EG1_{i,k}$: the distance separating the center of rotation OG from the plane $P2_i$, taking into account the eye/spectacles distance VG1;

$EG2_{i,k}$: the distance separating the center of rotation OG from the plane $P2_i$, taking into account the eye/spectacles distance VG2; and $EG3_{i,k}$: the distance separating the center of rotation OG from the plane $P2_i$, taking into account the eye/spectacles distance VG3.

These values may then be reinserted into the initial formulae in order to continue the iteration.

The iterative calculation stops either after a preset number of iterations (for example k=3), or when in two successive iterations the values of $EG1_{i,k}$ and $EG1_{i,k+1}$, those of $EG2_{i,k}$ and $EG2_{i,k+1}$ and those of $EG3_{i,k}$ and $EG3_{i,k+1}$ are similar (namely here within 0.1 mm).

The values of $EG1_{i,k}$, $EG2_{i,k}$, $EG3_{i,k}$ obtained are then considered as being the simulated half pupillary distances $EG1_i$, $EG2_i$, $EG3_i$.

Once all of the simulated half pupillary distances $EG1_i$, $EG2_i$, $EG3_i$ have been calculated, the processing unit 250 selects, from the simulated eye/spectacles distances VG1, VG2, VG3, the distance that is closest to the actual value VG.

To do this, the processing unit 250 determines, for each simulated eye/spectacles distance VG1, VG2, VG3, the standard deviation $\sigma_1$, $\sigma_2$, $\sigma_3$ of the associated simulated half pupillary distances $EG1_i$, $EG2_i$, $EG3_i$.

By way of example, the standard deviation $\sigma_1$ associated with the first simulated eye/spectacles distance VG1 is equal to the standard deviation of the simulated half pupillary distances $EG1_{303}$, $EG1_{302}$, $EG1_{303}$.

Thus, the selected simulated eye/spectacles distance VG2 is that for which the standard deviation $\sigma_2$ is the lowest.

The processing unit 250 then considers that this simulated eye/spectacles distance VG2, once scaled, is equal to the actual eye/spectacles distance VG of the wearer 1. It therefore stores its value in memory.

The processing unit 250 then calculates the mean of the simulated half pupillary distances $EG2_{301}$, $EG2_{302}$, $EG2_{303}$ associated with this selected simulated value VG2.

It then considers that this mean, once scaled, is equal to the left half pupillary distance EG of the wearer 1. It therefore stores its value in memory.

The right eye/spectacles distance VD and the right half pupillary distance ED of the wearer 1 may then be determined in the same way as for the left eye/spectacles distance VG and the left half pupillary distance EG of the wearer 1.

In a subsequent operation, the processing unit 250 calculates the pupillary heights HG, HD of the wearer 1 (see FIG. 1).

Once again, the processing unit 250 may proceed in various ways.

Here, the pitch of the head 10 of the wearer 1 is considered to have little impact on the precision of the pupillary heights HG, HD that may be measured in the images 301, 302, 303.

Therefore, to determine these pupillary heights, the processing unit 250 selects any one of the images 301, 302, 303 (for example that for which the yaw angle $\alpha_{302}$ is the smallest) then determines in this image 302 (FIG. 6) the distances $HG_{302}$, $HD_{302}$ separating each of the corneal reflections 162G, 162D from the lower edge of the corresponding boxing-system box 151G, 151D.

These distances $HG_{302}$, $HD_{302}$, once scaled, are then stored in memory by the processing unit 250 as being the pupillary heights HG, HD.

As a variant, the processing unit will possibly measure these distances $HG_i$, $HD_i$ in each of the images 301, 302, 303, average these distances and scale them in order to obtain the pupillary heights of the wearer.

As another variant, the pupillary heights will possibly be calculated using a method analogous to that used to determine the half pupillary distances of the wearer. This method will for example consist in acquiring various images of the wearer nodding their head to say "yes", in determining the pitch angles of the head in each of these images, and in measuring the pupillary heights in the image for which the pitch angle is smallest.

The following operation consists, for the processing unit 250, in determining the propensity of the wearer 1 to turn their gaze by moving rather their head 10 or their eyes 20G, 20D.

The vendor then explains to the wearer 1 that he or she must look at the first additional target 320, then, once the latter is turned off and the second additional target 330 is turned on, that he or she must rapidly turn their gaze toward this second additional target 330.

Once the wearer 1 is ready, the vendor initiates a new series of measurements by pressing on an ad hoc button displayed on the touchscreen 270.

The processing unit 250 then turns on only the first additional target 320, for about 5 seconds, then turns off the first additional target 320 and simultaneously turns on the second additional target 330. At the moment when the first additional target 320 is turned off, the processing unit 250 acquires and stores in memory a plurality of images (10 for example) during a sequence of about 1 second.

The acquired images are then processed by the processing unit 250 in order to determine, in each of them, the yaw angle $\alpha_i$ of the head 10 of the wearer 1.

If, in the 10 acquired images, this angle varies little and/or slowly, the processing unit 250 determines that the wearer has a propensity to turn their gaze by moving rather their eyes 20G, 20D.

In contrast, if, in the 10 acquired images, this angle varies a lot and/or rapidly, the processing unit 250 determines that the wearer has a propensity to turn their gaze by moving rather their head 10.

As a variant, the processing unit could proceed in another way.

By way of example, a more refined approach could be used, the distances $EG_i$, $ED_i$ separating the corneal reflections 162D, 162G from the observable axis A3 also being determined in each acquired image.

The processing unit could then compare the speeds and/or amplitudes of variation in the yaw angle $\alpha_i$ with the speeds and/or amplitudes of variation in the distances $EG_i$, $ED_i$. It could thus deduce therefrom whether the wearer has a propensity to turn their eyes or head more rapidly. It could even deduce therefrom a refined coefficient, quantifying the propensity of the wearer to turn their gaze by moving rather their head or their eyes.

Following these various operations, the processing unit 250 has acquired:

- a scanned image of the prescriptions of the wearer;
- the model of the spectacle frame selected by the wearer 1;
- the half pupillary distances EG, ED of the wearer 1;
- the pupillary heights HG, HD of the wearer 1;
- a visible image of the face of the wearer 1;
- the distances VG2, VD2 separating the centers of rotation of the eyes of the wearer 1 and the midplane P1 of the spectacle frame 110; and
- a coefficient quantifying the propensity of the wearer 1 to turn their gaze by moving rather their head 10 or their eyes 20G, 20D.

It then displays these various pieces of information on the touchscreen 270 so that they can be verified by the vendor.

After validation by the vendor, the processing unit 250 has this information printed on a summarizing sheet. The processing unit then communicates this information to the center for manufacturing ophthalmic lenses.

Optionally, provision will possibly be made for the processing unit 250 to furthermore communicate all of the acquired images to the center for manufacturing ophthalmic lenses.

Thus, the processing center will optionally be able to carry out an operation for verifying all the data calculated by the processing unit 250.

These data will possibly be verified in particular when the software package installed in the processing unit 250 is not up-to-date.

They will also possibly be verified when the selected frame is a "rimless" frame. This is because the edges of the display lenses of these frames are generally difficult to see in the acquired images, which may generate errors.

This verifying operation will possibly be carried out automatically (especially in the case where the software package is not up-to-date), or manually, by a specialist technician who will possibly in particular verify that the pupils and the edges of the display lenses have been correctly located.

The present invention is in no way limited to the embodiments described and shown, and those skilled in the art will be able to make modifications thereto without departing from the scope of the invention.

In particular, provision will possibly be made for the measuring device to take, rather than the form of a kiosk housing the processing unit, the image sensor and the light sources, a smaller, portable form. Thus, provision will possibly be made for the processing unit to be formed by a portable computer in which an ad hoc software package will be installed, and the video camera (or "web-cam") of which will play the role of the video camera in the visible domain. In this variant, the infrared video camera and the light source will then be arranged in a small housing equipped with a clip for fastening to the screen of the portable computer and a cable for connecting to the portable computer. This solution will be inexpensive and easily transportable.

According to another variant embodiment of the invention, provision will possibly be made for the processing unit to merely capture images and communicate them to the center for manufacturing ophthalmic lenses, in which case these images will be processed in this manufacturing center.

The invention claimed is:

1. A device for determining at least one characteristic for optimizing the wear position of a pair of spectacles on the face of a wearer, said optimizing characteristic being a geometrico-morphological, postural or behavioral characteristic, the device comprising:
    at least one infrared light source configured to illuminate at least part of the head of said individual;
    an infrared image sensor configured to acquire an image of at least part of the head of said individual illuminated by the infrared light source; and
    a processing unit programmed to execute the following steps: locate, on said image, largest reflections of the infrared light source reflected by two lenses of the pair of spectacles and at least one corneal reflection of the infrared light source reflected by one of the two eyes of the wearer, and deduce said geometrico-morphological, postural or behavioral characteristic depending on:
        the distances separating an observable axis from the centers of the two largest reflections, and
        the position of said corneal reflection in said image.

2. The determining device as claimed in claim 1, wherein the processing unit is a central processing unit of a computer, and the infrared light source and the infrared image sensor are separate from the central processing unit and include a communication system configured to communicate with the central processing unit of the computer.

3. The determining device as claimed in claim 1, further comprising a single light source movably mounted relative to said image sensor or for at least two light sources that are distant from each other in order to generate two separate reflections on said image.

4. The determining device as claimed in claim 1, wherein the at least one infrared light source is composed of at least one light-emitting diode.

5. The determining device as claimed in claim 1, wherein the infrared image sensor is configured to acquire images in the visible domain.

6. The determining device as claimed in claim 5, further comprising one or more of a display system configured to display the images acquired in the visible domain, and a printing system configured to print the images acquired in the visible domain.

7. The determining device as claimed in claim 1, further comprising a visible image sensor that is separate from the infrared image sensor and that is configured to acquire an image of the wearer in the visible domain.

8. The determining device as claimed in claim 7, further comprising one or more of a display system configured to display the images acquired in the visible domain, and a printing system configured to print the images acquired in the visible domain.

9. The determining device as claimed in claim 1, further comprising an acquisition system configured to acquire at least one dimension of the pair of spectacles.

10. The determining device as claimed in claim 1, further comprising a supporting structure to which the infrared light source, the infrared image sensor, and the processing unit are securely fastened.

11. The determining device as claimed in claim 10, wherein the supporting structure includes a mounting and a slide that is movably mounted on the mounting and that supports the infrared light source or the infrared image sensor.

12. The determining device as claimed in claim 11, wherein the mobility of the slide is motorized, and said processing unit is configured to automatically control a position of the slide such that the face of said individual is visible to the infrared image sensor.

13. A method for determining at least one characteristic for optimizing the wear position of a pair of spectacles on the face of a wearer, said optimizing characteristic being a geometrico-morphological, postural or behavioral characteristic, the pair of spectacles including a frame and two lenses, the method including steps of:
    a) illuminating at least part of the head of the wearer using an infrared light source;
    b) acquiring, via an infrared image sensor, an image of the head of the wearer illuminated by the infrared light source, in which image the pair of spectacles and the eyes of the wearer appear;
    c) locating, in the image acquired in step b), largest reflections of the infrared light source reflected by the two lenses of the pair of spectacles and at least one corneal reflection of the infrared light source reflected by one of the two eyes of the wearer; and
    d) deducing by a processing unit said geometrico-morphological, postural or behavioral characteristic depending on:
        the distances separating an observable axis from the centers of the two largest reflections, and
        the position of said corneal reflection in said image.

14. The determining method as claimed in claim 13, wherein
- in step b), the infrared image sensor acquires at least two images of the head of the wearer,
- in step c), said reflections are located in each image acquired in step b), and
- in step d), the behavioral characteristic is deduced from the positions of said reflections and includes a coefficient quantifying the propensity of the wearer to turn the gaze of the wearer by moving either the head of the wearer or the eyes of the wearer.

15. The determining method as claimed in claim 13, wherein, in step d)
- said postural characteristic is deduced depending on the positions of the reflections in said image, and
- said geometrico-morphological characteristic is deduced depending on the positions of said corneal reflection in said image and on said postural characteristic.

16. The determining method as claimed in claim 13, wherein in step c), in the image acquired in step b), the corneal reflections of the infrared light source reflected by both eyes of the wearer are located.

17. The determining method as claimed in claim 13, wherein in step b), said image is acquired in the domain of the near infrared, with a wavelength included between 780 and 1400 nm.

18. The determining method as claimed in claim 13, wherein said postural characteristic includes a yaw angle, which separates the sagittal plane of the head of the wearer and the optical axis of the infrared image sensor.

19. The determining method as claimed in claim 13, wherein said geometrico-morphological characteristic includes the half pupillary distances of the wearer.

20. The determining method as claimed in claim 13, wherein said geometrico-morphological characteristic includes the pupillary heights of the wearer.

21. The determining method as claimed in claim 13, wherein said geometrico-morphological characteristic includes the positions of the centers of rotation of the eyes of the wearer.

* * * * *